United States Patent
Moss et al.

(10) Patent No.: US 9,004,915 B2
(45) Date of Patent: Apr. 14, 2015

(54) TABBED DENTAL APPLIANCE

(75) Inventors: Jon F. Moss, Antioch, CA (US); Rene M. Sterental, Palo Alto, CA (US)

(73) Assignee: Align Technology, Inc., San Jose, CA (US)

(*) Notice: Subject to any disclaimer, the term of this patent is extended or adjusted under 35 U.S.C. 154(b) by 159 days.

(21) Appl. No.: 13/018,771

(22) Filed: Feb. 1, 2011

(65) Prior Publication Data
US 2011/0123941 A1 May 26, 2011

Related U.S. Application Data

(63) Continuation of application No. 11/807,367, filed on May 25, 2007, now Pat. No. 7,878,805.

(51) Int. Cl.
*A61C 7/08* (2006.01)
*A61C 7/00* (2006.01)

(52) U.S. Cl.
CPC .. *A61C 7/08* (2013.01); *A61C 7/002* (2013.01)

(58) Field of Classification Search
CPC .......................................................... A61C 7/08
USPC ............................................. 433/6, 18, 24, 7
See application file for complete search history.

(56) References Cited

U.S. PATENT DOCUMENTS

| | | | |
|---|---|---|---|
| 4,139,944 A | 2/1979 | Bergersen | |
| 4,253,828 A * | 3/1981 | Coles et al. | 433/6 |
| 4,830,612 A | 5/1989 | Bergersen | |
| 5,876,199 A | 3/1999 | Bergersen | |
| 6,435,871 B1 * | 8/2002 | Inman | 433/7 |
| 2003/0224313 A1 | 12/2003 | Bergersen | |
| 2003/0224314 A1 | 12/2003 | Bergersen | |
| 2004/0058295 A1 | 3/2004 | Bergersen | |
| 2004/0170941 A1 * | 9/2004 | Phan et al. | 433/6 |
| 2006/0084024 A1 | 4/2006 | Farrell | |
| 2006/0099545 A1 | 5/2006 | Lai et al. | |
| 2006/0110698 A1 * | 5/2006 | Robson | 433/6 |
| 2006/0188834 A1 * | 8/2006 | Hilliard | 433/24 |
| 2007/0178420 A1 | 8/2007 | Keski-Nisula et al. | |

OTHER PUBLICATIONS

International Search Report and Written Opinion from related PCT Application PCT/US2008/006491, dated Sep. 23, 2008, 8 pages.

* cited by examiner

*Primary Examiner* — Ralph Lewis
(74) *Attorney, Agent, or Firm* — Brooks, Cameron & Huebsch, PLLC

(57) ABSTRACT

Embodiments include dental appliances, dental appliance systems, and methods of making and using such appliances. In one embodiment, a dental appliance includes a number of tooth apertures for the placement of teeth therein and a tab representing a position of a tooth that has not fully erupted and oriented to be received over the position of the tooth that has not fully erupted.

15 Claims, 4 Drawing Sheets

TABBED DENTAL APPLIANCE

PRIORITY INFORMATION

This application is a Continuation of U.S. application Ser. No. 11/807,367, filed May 25, 2007, the specification of which is incorporated herein by reference.

BACKGROUND

The present disclosure is related generally to the field of orthodontics. More particularly, the present disclosure is related to the field of dental alignment which can be utilized where teeth have not fully erupted.

Many orthodontic treatments involve repositioning misaligned teeth and changing bite configurations for improved cosmetic appearance and dental function. Repositioning can be accomplished, for example, by applying controlled forces to one or more teeth over a period of time.

Some orthodontic processes use dental positioning appliances for realigning teeth. Such appliances may utilize a thin shell of material having resilient properties, referred to as an "aligner" that generally conforms to a patient's teeth but is slightly out of alignment with the initial tooth configuration.

Placement of such an appliance over the teeth provides controlled forces in specific locations to gradually move the teeth into a new configuration. Repetition of this process with successive appliances that provide progressive configurations eventually move the teeth through a series of intermediate arrangements to a final desired arrangement. An example of such a system is described in U.S. Pat. No. 5,975,893.

Such systems generally rely on designing and fabricating some, most, or all of the appliances, to be worn by the patient, at the outset of treatment. In some processes the design of the appliances relies on computer modeling of a series of successive tooth arrangements and the individual appliances are designed to be worn over the teeth and to reposition the teeth by using the appliances in a serial order, progressing from a first appliance, through each of the intermediate appliances, to the last appliance.

However, in some instances, the patient has teeth that are not fully erupted (i.e. vertically positioned). In such instances, these teeth can supra-erupt creating interferences with the opposite arch or suffer other alignment problems since they are not included in the treatment plan. Since the teeth are at the commencement of treatment, in many cases, much lower that the other teeth, the appliances are not designed to accommodate such teeth.

DETAILED DESCRIPTION

Embodiments include dental appliances, dental appliance systems, and methods of making and using such appliances and systems. In some embodiments, for example, a dental appliance can include one or more tooth apertures for the placement of teeth therein and a tab representing a position of a tooth that has not fully erupted.

Such a tab can, for instance, be oriented to be received over the position of the tooth that has not fully erupted. In this way, the tab can provide force and/or support to one or more other teeth being adjusted, even though the tooth is not fully in position, among other benefits. This can be particularly useful in adjusting teeth that are adjacent to (e.g., above or next to) the not fully erupted tooth. Another benefit of such an appliance is that force can be applied to one or more teeth that are erupting in order to keep the teeth from over erupting (e.g., supra-eruption).

Figure 3A:
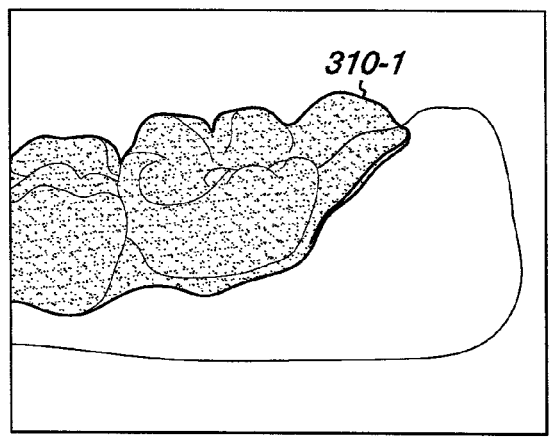
FIG. 3A illustrates another example of an appliance end having a small tab provided thereon according to an embodiment of the present disclosure.
Figure 3B:
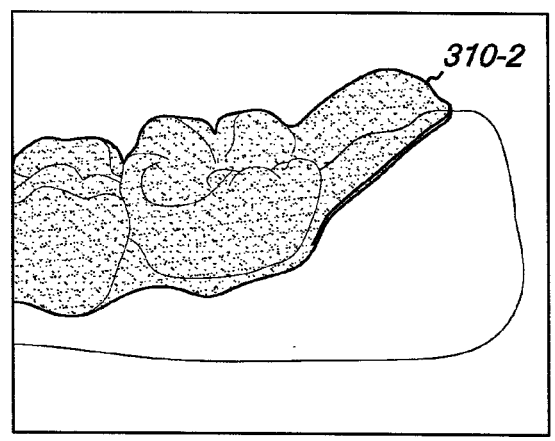
FIG. 3B illustrates an example of an appliance end having a medium sized tab provided thereon according to an embodiment of the present disclosure.
Figure 3C:
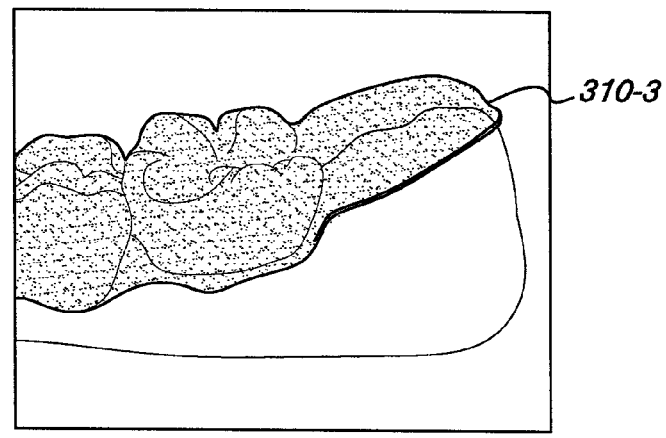
FIG. 3C illustrates an example of an appliance end having a large sized tab provided thereon according to an embodiment of the present disclosure.

In some embodiments, the tab can be of a length to span (i.e., extend) across a portion of a horizontal position (e.g., in the middle of a number of teeth or at the end of a number of teeth) to be occupied by the tooth when fully erupted. Embodiments of such configurations are illustrated in FIGS. 3A-3C, among others. For instance, as illustrated in FIG. 3B, the tab can be of a length to span across half of the horizontal position to be occupied by the tooth when fully erupted.

Embodiments of the present disclosure also include a number of method embodiments. For example, in some embodiments, a method can include applying a first dental appliance of a number of appliances shaped to move teeth by inserting the first appliance into a mouth of a patient, where the first dental appliance has a tab of a first length representing a position of a tooth that has not fully erupted and applying a second dental appliance of the number of appliances, where the second dental appliance has a tab of a second length representing a position of a tooth that has not fully erupted and where the tab of a second length is longer than the tab of the first length.

In some embodiments, a first aligner can include a small sized tab and a subsequent aligner can include a larger sized tab. The use of different aligner sizes can be utilized for a number of different reasons. Such embodiments can be beneficial, for example, to provide better patient comfort than a full sized aligner.

For example, if a molar has not fully erupted, it may be uncomfortable to wear a full sized aligner with a molar aligner portion provided thereon since the portion protrudes past the teeth that are fully erupted. Less than full length tabbed aligners can be beneficial, in some instances, because the tab can reduce or prevent supra-eruption if a tooth erupts into contact with the tab during use of the tabbed aligner, among other benefits.

Such embodiments can also be beneficial because a longer tab length can provide more rigidity and/or can be shaped to receive one or more surfaces of an erupting tooth, among other benefits and functions. In some embodiments, the length of the tabs can remain the same from one aligner to a subsequent one or can change from a larger tab to a smaller tab from one aligner to a subsequent one.

As discussed above, embodiments can include removing the first appliance before inserting the second appliance. This can be beneficial in implementing embodiments utilizing successive stages of arrangements to adjust positions of one or more teeth.

In some such embodiments, one or more dental appliances can be applied. In such embodiments, a third dental appliance, for example, can have a tab of a length representing a position of a tooth that has not fully erupted and where the tab of such length is longer than the tabs of the first and second lengths.

Such embodiments can be beneficial, for example, as the erupting tooth continues to erupt and can, in some instances, begin to be used for support of the other portions of the appliance to which the tab is attached and/or to other appliances, the application of force, and/or can begin to be adjusted, among other benefits. For example, the aligner tab can be used to apply force to one or more teeth being moved by the aligner or an adjacent aligner.

Tabs can also be designed to provide some initial adjustment to an erupting tooth as it is erupting. Such embodiments can be beneficial where a tooth may be erupting in an incorrect position and may be able to keep an erupting tooth from affecting the positioning of other teeth, if the erupting tooth is erupting in a manner to produce such an affect.

In some embodiments, a third dental appliance can have a tab of a length representing a position of a tooth that has fully erupted. In such embodiments, the tab of such length will likely be longer than the tabs of the first and second lengths. In this way, the tab can use one or more surfaces of the erupted tooth to aid in providing support, force, and/or its position can be adjusted.

In some embodiments, the first appliance can be removed when the tooth that has not fully erupted reaches a threshold of eruption. Thresholds of eruption can be any suitable threshold, and may be determined by the manufacturer or by a treatment professional.

For example, a threshold for removing a first appliance may be when the top of the tooth erupts from the surface of the gingiva. A threshold for removing a second appliance may be when the tooth has erupted past a halfway point as determined by a treatment professional, for example.

In some embodiments, a first dental appliance of a number of appliances can be designed by surveying the positioning of a patient's teeth within a mouth of a patient, where the first dental appliance has a tab of a first length representing a position of a tooth that has not fully erupted. Such an embodiment, may also include a second dental appliance of the number of appliances that is designed having a tab of a second length representing a position of a tooth that has not fully erupted and where the tab of a second length is longer than the tab of the first length.

In such embodiments, the surveying of the positioning of a patient's teeth within a mouth of a patient can, for example, be accomplished by taking a set of one or more data points manually by a treatment professional and entering the data points into a computing device.

The data can also be obtained through an automated or semi-automated process. Further, a size and/or shape of an erupting tooth can be estimated, for example, through use of a library of teeth sizes and/or shapes and/or information about the patient's other teeth. This information can be provided manually by a treatment professional or by an automated or semi-automated process in various embodiments.

Figure 1:
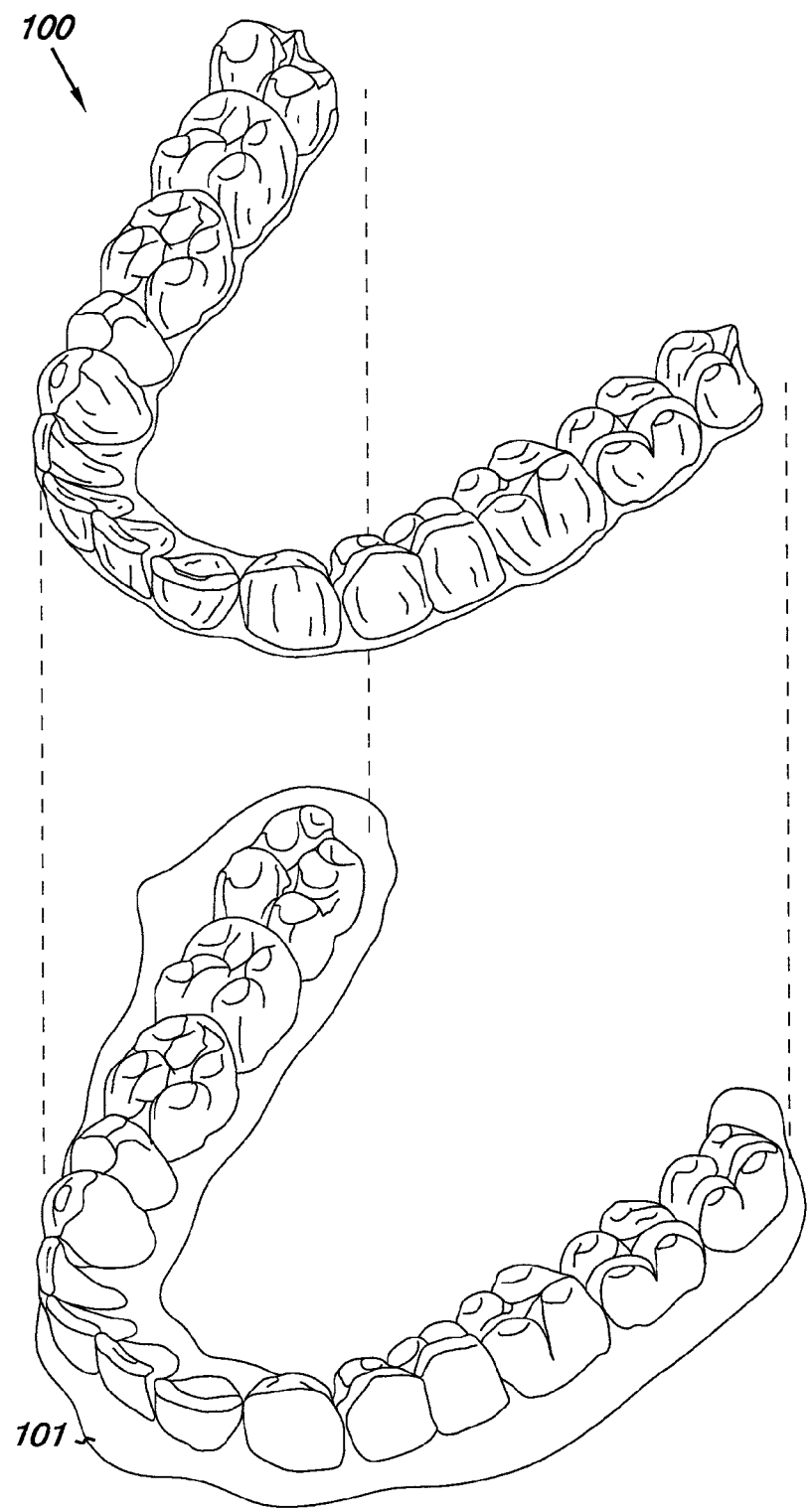
FIG. 1 illustrates a jaw of a subject together with an example of a tabbed position adjustment appliance embodiment of the present disclosure.

Referring now to FIG. 1, FIG. 1 illustrates a jaw of a subject together with an example of a tabbed position adjustment appliance embodiment of the present disclosure. In various embodiments, such appliances can be used to affect incremental repositioning of one or more teeth, as described generally above.

The processes or systems of the present disclosure can employ any positioners, retainers, and/or other removable appliances for finishing and maintaining teeth positions in connection with orthodontic treatment. The systems for use with embodiments of the present disclosure can utilize a plurality of such appliances that can, for example, be worn by a patient successively in order to achieve the gradual tooth repositioning, as described herein.

An appliance (e.g., appliance 100) can, for example, be fabricated from a polymeric shell, or formed from other material, having a cavity shaped to receive and apply force to reposition teeth from one teeth arrangement to a successive teeth arrangement. The shell may be designed to fit over a number of, in many instances all teeth, present in the upper or lower jaw 101.

In some situations, certain individual or small sets of the teeth will be repositioned while others of the teeth will provide a base or anchor region for holding the repositioning appliance in place as it applies a resilient repositioning force against the tooth or teeth to be repositioned. In such cases, one or more of the teeth which are moved can also serve as a base or anchor region for holding the repositioning appliance. Additionally, the gums and/or the palette can serve as an anchor region, thus allowing all or nearly all of the teeth to be repositioned at the same time, if desired.

Figure 2A:
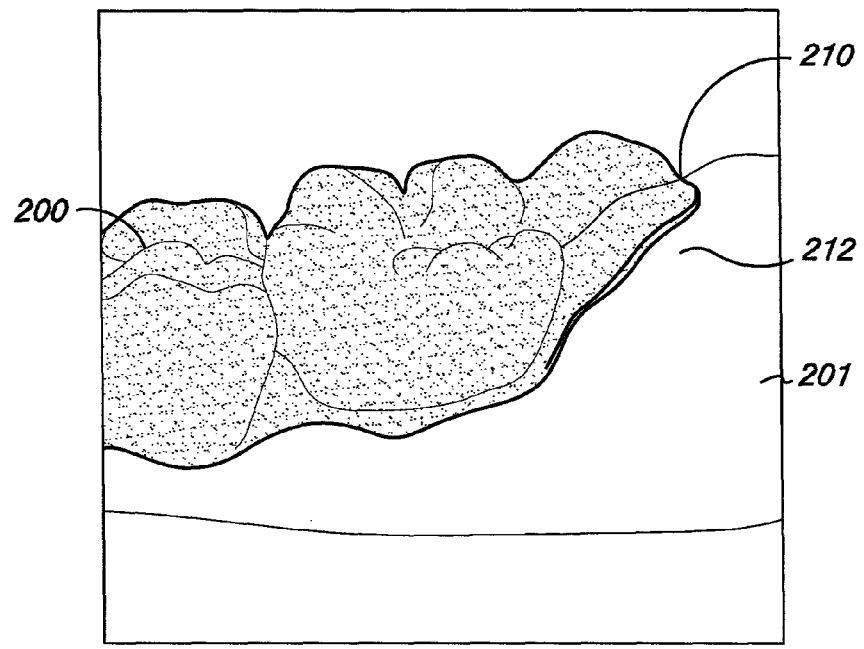
FIG. 2A illustrates an example of an appliance end having a small tab provided thereon according to an embodiment of the present disclosure.

FIG. 2A illustrates an example of an appliance end having a small tab provided thereon according to an embodiment of the present disclosure. In FIG. 2A, the appliance embodiment has been positioned over the teeth and the illustration is focused on the positioning of one end of the appliance that includes a small sized tab thereon.

For example, in the embodiment of FIG. 2A, the tab 210 extends over the mesial cusps of the erupting tooth 212 which is covered by the gingiva on the jaw 201. The amount that the tab extends can be any length (i.e., a horizontal extension to cover a portion of a top or side of a tooth surface).

Additionally, tabs can also have different depths (i.e., a portion of a tab that extends vertically along one or more side surfaces of a tooth) and/or thicknesses (i.e., the thickness of the material that forms a horizontal or vertical surface of the tab). For example, the depth of the tab can be any depth, from virtually no depth (i.e., the thickness of the material forming a horizontal tab portion) to a depth of the bottom of a side tooth surface (i.e., a depth above or below the gingiva).

In some embodiments, the thickness of one or more surfaces of the tab can be increased to create contact with the erupting tooth. In some embodiments, a surface of the tab can be oriented to be placed in contact with the tooth. For example, if a bottom surface of a tab is to be positioned to contact a top surface of a tooth, the horizontal surface that forms the bottom surface of the tab can be positioned lower than those horizontal surfaces forming the other portions of the aligner that are oriented to contact top surfaces of teeth that are fully erupted (e.g., stepped down from one or more other surfaces of the aligner). In some embodiments, at least one of a depth or thickness of a surface on a first dental appliance can be greater than a corresponding surface on the second dental appliance. Such thickened or stepped embodiments can be beneficial in instances where the aligner is used to aid in the positioning of a tooth as it is erupting.

In some embodiments, the depth or thickness of a tab can be adjusted from one aligner to a subsequent aligner. For example, an aligner may have a first thickness and/or depth that is thicker and/or deeper than a subsequent aligner. This may be due to the amount that the tooth has erupted or the positioning of the aligner with respect to the gingiva adjacent to the tooth that is erupting.

Although illustrated in FIG. 2A as oriented to abut the top surface of the erupting tooth, one or more tabs may be provided on an appliance that will abut one or more side surfaces of the erupting tooth. Tabs may also be provided that are designed to abut multiple surfaces on the erupting tooth. For example, in some embodiments, a tab may have a bottom surface that will abut the top surface of a tooth and a side surface that will abut the side surface of a tooth.

As discussed herein, the one or more tabs may be designed to be positioned to abut a tooth surface as the tooth erupts further from its current position or may be designed to be positioned in a location that would abut a fully erupted tooth, but when positioned initially, may not abut any tooth surface. Further, as discussed herein a number of appliances with tabs of varying shapes and lengths can be provided to provide support, force, and/or alignment of the erupting tooth and/or other teeth, such as those abutting surfaces of the appliance to which the tab is attached or other appliances.

Figure 2B:
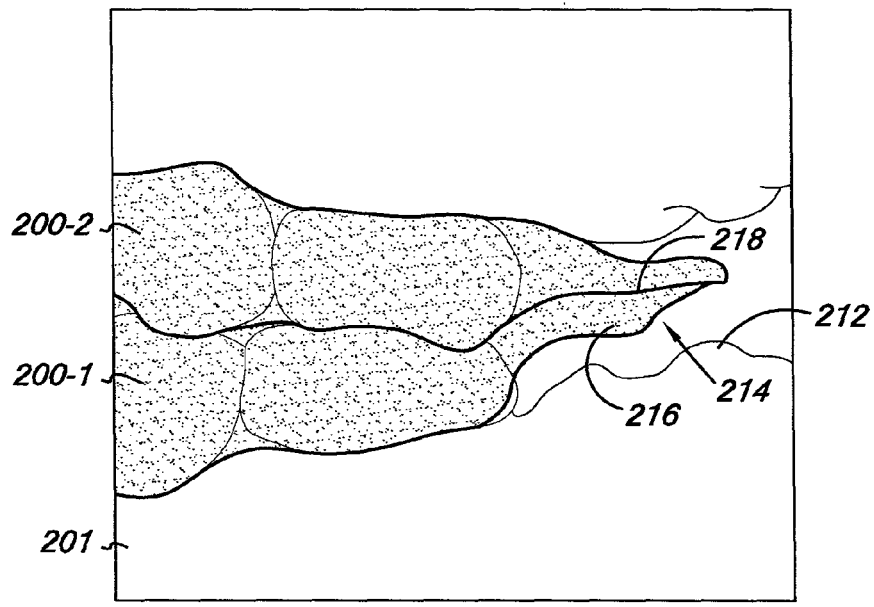
FIG. 2B illustrates an example of upper and lower appliance ends each having a small tab provided thereon according to an embodiment of the present disclosure.

FIG. 2B illustrates an example of upper and lower appliance ends each having a small tab provided thereon according to an embodiment of the present disclosure. In the embodiment of FIG. 2B, a first appliance 200-1 and a second appliance 200-2 are designed to have a mating engagement such that proper forces are exerted for alignment of a number of teeth.

In the embodiment illustrated in FIG. 2B, the second appliance has a tab with a bottom surface 214, a side surface 216, and a top surface 218. The bottom surface 214 is shaped to accommodate the shape of the top of the erupting tooth 212 within the gingiva of the jaw 201. The side surface 216 is shaped to accommodate the shape of one side of the erupting tooth 212.

In some embodiments, the tab includes a surface that is shaped to mate with one or more surfaces of another appliance to be positioned adjacent to the surface of the tab. Such surfaces can be used to provide support, force, and/or adjustment to one or more teeth being adjusted by the first and/or second appliance, among other benefits.

For example, in various embodiments, the tab can include a surface that is shaped to mate with a surface of a second tab of a second appliance that is to be positioned adjacent to the surface of the tab. As discussed above, such surfaces can be used to provide support, force, and/or adjustment to one or more teeth being adjusted by the first and/or second appliance, among other benefits.

For instance, in the embodiment of FIG. 2B, the top surface 218 is shaped to mate with a surface of the appliance 200-2 (e.g., the tab portion thereof, for example). The terms top and bottom are used herein to aid the reader and are not to be viewed as limiting with respect to the embodiments of the present disclosure.

Embodiments of the present disclosure also include a number of dental appliance system embodiments. For example, in some embodiments, a system can include a first dental appliance of a number of appliances shaped to move teeth.

The first appliance can, for instance, include a tab of a first length representing a position of a tooth that has not fully erupted. The system can also include a second dental appliance of the number of appliances, where the second dental appliance has a tab of a second length representing a position of a tooth.

In such embodiments, the first appliance can be an appliance for adjustment of upper teeth of a patient and the second appliance can be for the adjustment of lower teeth of the patient, in some embodiments. In various embodiments, the appliances can be used on different teeth in the upper or lower portion of the patient's mouth.

Additionally, in some embodiments, the appliances can be used serially in the patient's mouth (i.e., one appliance is removed from a patient's mouth and another appliance is positioned therein). Such embodiments can be used sequentially, for example, as part of a system of adjustment that moves one or more teeth through a number of successive stages of arrangements, such as incrementally moving teeth from an initial position through a number of intermediate positions and then to a final position.

For instance, in the embodiments represented in FIGS. 3A, 3B, and 3C, the appliances can be used as a system. FIG. 3A illustrates an example of an appliance end having a small tab provided thereon according to an embodiment of the present disclosure, similar to that provided in the embodiment of FIG. 2A.

FIG. 3B illustrates an example of an appliance end having a medium sized tab provided thereon according to an embodiment of the present disclosure. In the embodiment of FIG. 3B, the tab can, for example, span midway across the area over which a tooth is erupting. A medium tab can be any size and shape between a small tab and a large tab.

For example, in some embodiments, the medium tab length can be designed to cover the mesial cusps and a portion of (e.g., half of) the distal cusps. Additionally, in some embodiments, there can be several differently sized medium tab appliances between the small and large tab appliances. In some embodiments, the tab can have multiple medium sized surfaces. For example, the tab can include one or more side surfaces that are sized between the small tab and the large tab appliances.

In some embodiments, the tab can be of a length to span across the entire horizontal position to be occupied by the tooth when fully erupted. In some such embodiments, the tab can have a number of surfaces constructed to interact with the surface of the tooth when partially and/or fully erupted.

For example, FIG. 3C illustrates an example of an appliance end having a large sized tab provided thereon according to an embodiment of the present disclosure. For instance, in various embodiments, the tab includes a bottom surface that is shaped to mate with a top surface of the tooth. In the embodiment of FIG. 3C, the tab extends over the entire occlusal surface of the erupting/erupted tooth.

In some embodiments, the tab includes a bottom surface that is shaped to mate with a top surface of the tooth when fully erupted. In such embodiments, the tooth can potentially erupt into position within the shape of the tab and, therefore, the tab can be used to provide support, force, and/or adjustment to the erupting/erupted tooth and/or other teeth that are being adjusted by the one or more appliances.

In various embodiments, the tab can be a side surface that is shaped to mate with a side surface of the tooth. Such a side surface can also be a part of a tab, as discussed above.

Figure 4:
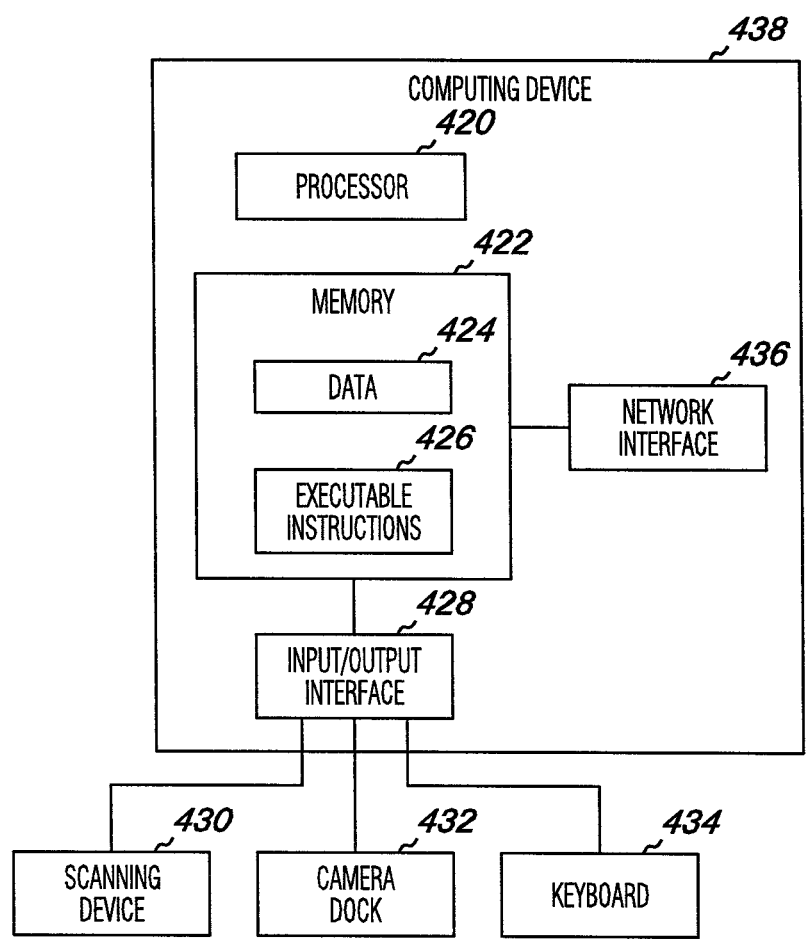
FIG. 4 provides a computing system for use in the design of dental appliances thereof that can be used in association with the fabrication of embodiments of the present disclosure.

FIG. 4 provides a computing system for use in the design of dental appliances thereof that can be used in association with the fabrication of embodiments of the present disclosure. In the system illustrated in FIG. 4, the system includes a computing device 438 having a processor 420 and memory 422. The memory can include various types of information including data 424 and executable instructions 426 as discussed herein.

Additionally, as illustrated in the embodiment of FIG. 4, a system can include a network interface 436. Such an interface can allow for processing on another networked computing device or such devices can be used to obtain information about the patient or executable instructions for use with various embodiments provided herein.

As illustrated in the embodiment of FIG. 4, a system can include one or more input and/or output interfaces 428. Such interfaces can be used to connect the computing device with one or more input or output devices. For example, in the embodiment illustrated in FIG. 4, the system includes connectivity to a scanning device 430, a camera dock 432, and a keyboard.

Such connectivity allows for the input of image information (e.g., scanned images or digital pictures, etc.) or instructions (e.g., input via keyboard) among other type of information. Although some embodiments may be distributed among various computing devices within one or more networks, such systems as illustrated in FIG. 4 can be beneficial in allowing for the capture, calculation, and analysis of the various information discussed herein.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the disclosure.

It is to be understood that the use of the terms "a", "an", "one or more", "a number of", or "at least one" are all to be interpreted as meaning one or more of an item is present. Additionally, it is to be understood that the above description has been made in an illustrative fashion, and not a restrictive one. Combination of the above embodiments, and other embodiments not specifically described herein will be apparent to those of skill in the art upon reviewing the above description.

The scope of the various embodiments of the disclosure includes any other applications in which the above structures and methods are used. Therefore, the scope of various embodiments of the disclosure should be determined with reference to the appended claims, along with the full range of equivalents to which such claims are entitled.

In the foregoing Detailed Description, various features are grouped together in a single embodiment for the purpose of streamlining the disclosure. This method of disclosure is not to be interpreted as reflecting an intention that the embodiments of the disclosure require more features than are expressly recited in each claim.

Rather, as the following claims reflect, inventive subject matter lies in less than all features of a single disclosed embodiment. Thus, the following claims are hereby incorporated into the Detailed Description, with each claim standing on its own as a separate embodiment.

What is claimed:

1. A dental appliance for use with a tooth that is not fully erupted, comprising:
   a shell having a number of tooth apertures configured to receive and reposition a number of teeth of only one of an upper jaw or a lower jaw, wherein the number of tooth apertures each include a tooth contact surface shaped to mate with a portion of a coronal surface of a respective one of the number of teeth; and
   a tab directly connected to one of the number of tooth apertures and configured to extend in a distal direction along only one of a lingual, palatal, or facial side surface of a molar tooth of the one of the upper jaw or the lower jaw that has not fully erupted when the molar tooth that has not fully erupted is fully erupted, wherein the tab includes a tooth contact surface shaped to mate with only a portion of the side surface of the molar tooth that has not fully erupted extending between a patient's gingiva and a coronal surface of the molar tooth that has not fully erupted, wherein the tab defines a distal terminal end of the dental appliance, and wherein the dental appliance is configured to extend along only one of the lingual, palatal, or facial side surface of the molar tooth that has not fully erupted.

2. The dental appliance of claim 1, wherein the tab does not include a surface corresponding to a coronal surface of the molar tooth that has not fully erupted.

3. The dental appliance of claim 1, wherein the number of tooth apertures include side surfaces that are configured to extend substantially to the patient's gingiva.

4. The dental appliance of claim 1, wherein the tab includes a surface that is shaped to mate with a surface of a different tab positioned adjacent to the surface of the tab.

5. The dental appliance of claim 1, wherein the number of tooth apertures include side surfaces that are configured to extend toward the patient's gingiva.

6. The dental appliance of claim 1, wherein the tab is configured to provide adjustment to the molar tooth that has not fully erupted as it erupts.

7. A dental appliance for use with a tooth that is not fully erupted, comprising:
   a shell having a number of tooth apertures configured to receive and reposition a number of teeth of only one of an upper jaw or a lower jaw, wherein the number of tooth apertures each include a tooth contact surface shaped to mate with a portion of a coronal surface of a respective one of the number of teeth; and
   a tab directly connected to one of the number of tooth apertures and configured to extend in a distal direction along only one of a lingual, palatal, or facial side surface of a molar tooth of the one of the upper jaw or the lower jaw that has not fully erupted when the molar tooth that has not fully erupted is fully erupted, wherein the tab includes a tooth contact surface shaped to mate with a portion of a side surface of the molar tooth that has not fully erupted such that a coronal surface of the molar tooth that has not fully erupted extends beyond the tab when the molar tooth is fully erupted, wherein the tab defines a distal terminal end of the dental appliance, and wherein the dental appliance is configured to extend along only one of the lingual, palatal, or facial side surface of the molar tooth that has not fully erupted.

8. The dental appliance of claim 7, wherein the number of tooth apertures include side surfaces that are configured to extend substantially to a patient's gingiva.

9. The dental appliance of claim 7, wherein the tab includes a surface that is shaped to mate with a surface of a different tab positioned adjacent to the surface of the tab.

10. The dental appliance of claim 7, wherein the number of tooth apertures include side surfaces that are configured to extend toward a patient's gingiva.

11. The dental appliance of claim 7, wherein the tab is configured to provide adjustment to the molar tooth that has not fully erupted as it erupts.

12. A dental appliance for use with a molar tooth that is not fully erupted, comprising:
   a shell having a number of tooth apertures configured to receive and reposition a number of teeth of only one of an upper jaw or a lower jaw, wherein the number of tooth apertures each include a tooth contact surface shaped to mate with a portion of a coronal surface of a respective tooth of the number of teeth and a surface opposite the tooth contact surface shaped to mate with an outer surface of a second shell; and a tab directly connected to one of the number of tooth apertures and configured to extend in a distal direction along only one of a lingual, palatal, or facial side surface of the molar tooth of the one of the upper jaw or the lower jaw that has not fully erupted when the molar tooth is fully erupted, wherein the tab includes a tooth contact surface shaped to mate with a portion of a side surface of the molar tooth that has not fully erupted exclusive of a coronal surface of the molar tooth that has not fully erupted when the molar tooth that has not fully erupted is fully erupted, wherein the tab defines a distal terminal end of the dental appliance, and wherein the dental appliance is configured to extend along only one of the lingual, palatal, or facial side surface of the molar tooth that has not fully erupted.

13. The dental appliance of claim 12, wherein the number of tooth apertures include side surfaces that are configured to extend substantially to the patient's gingiva, wherein the number of tooth apertures are configured to receive a number of teeth from only one of an upper or lower jaw of the patient, and wherein the shell includes an outer surface opposite the number of tooth apertures that is shaped to match contours of the coronal surfaces of the teeth.

14. The dental appliance of claim 12, wherein the number of tooth apertures include side surfaces that are configured to extend toward the patient's gingiva.

15. The dental appliance of claim 12, wherein the tab is configured to provide adjustment to the molar tooth that has not fully erupted as it erupts.

* * * * *